(12) United States Patent
Wong (10) Patent No.: US 7,124,760 B2
(45) Date of Patent: Oct. 24, 2006

(54) TEMPLATE FOR THE LOCALIZATION OF LESIONS IN A BREAST AND METHOD OF USE THEREOF

(75) Inventor: Wilson S. Wong, Arcadia, CA (US)

(73) Assignee: Endocare, Inc., Irvine, CA (US)

( * ) Notice: Subject to any disclaimer, the term of this patent is extended or adjusted under 35 U.S.C. 154(b) by 760 days.

(21) Appl. No.: 10/150,344

(22) Filed: May 16, 2002

(65) Prior Publication Data

US 2003/0216750 A1 Nov. 20, 2003

(51) Int. Cl.
*A61B 19/00* (2006.01)

(52) U.S. Cl. ...................................... 128/897; 128/897
(58) Field of Classification Search ................ 128/897, 128/989, 898; 600/300, 407, 549, 587; 434/267; 602/41–57; 378/164

See application file for complete search history.

(56) References Cited

U.S. PATENT DOCUMENTS

| | | | |
|---|---|---|---|
| 2,821,703 A * | 1/1958 | Knauss ....................... 342/180 |
| 4,279,259 A | 7/1981 | Lee | |
| RE32,000 E | 10/1985 | Sagi | |
| 5,260,985 A * | 11/1993 | Mosby ....................... 378/164 |
| 5,301,681 A | 4/1994 | DeBan | |
| D348,618 S * | 7/1994 | Leslie et al. ................. D10/64 |
| 5,709,206 A | 1/1998 | Teboul | |
| 5,941,832 A | 8/1999 | Tumey | |
| 5,950,320 A | 9/1999 | Dorsey | |
| 6,122,544 A | 9/2000 | Organ | |
| 6,622,728 B1 * | 9/2003 | Rusin ......................... 128/897 |

* cited by examiner

*Primary Examiner*—Samuel G. Gilbert
(74) *Attorney, Agent, or Firm*—Lawrence N. Ginsberg (57) ABSTRACT

A template for the localization of lesions in a breast. The template includes a substrate of transparent material that includes a central marking; a horizontal line extending through the central marking; a first series of spaced lines, each line of the first series being perpendicular to the horizontal line and each line including marking indicia for indicating the distance of that line from the central marking; an oblique line extending approximately 45 degrees from the horizontal line and through the central marking; and, a second series of spaced lines, each line of the second series being perpendicular to the oblique line and each line including marking indicia for indicating the distance of that line from the central marking. There is a right breast template and a left breast template. The appropriate template is utilized and the CC and MLO views of a mammogram are used to define a CC line and an MLO line that are plotted on that template. The intersection of these two lines is indicative of the location of the lesion. The template can then be placed over the breast of the patient and a lesion-indicative marking can be placed on the patient's skin.

3 Claims, 6 Drawing Sheets

TEMPLATE FOR THE LOCALIZATION OF LESIONS IN A BREAST AND METHOD OF USE THEREOF

BACKGROUND OF THE INVENTION

1. Field of the Invention

This present invention relates to medical and scientific measuring devices, and more particularly to a template for precisely and efficiently localizing a lesion of the breast from mammogram results.

2. Description of the Related Art

Mammography has been shown to be the most sensitive and most reliable method to detect breast cancer. Mammograms are generally taken in two non-orthogonal projections for each breast. The "cranial caudal" (CC) projection is taken with the breast being compressed in superior to inferior orientation (vertically) with the x ray tube located in the superior aspect of the breast. The second projection is the "medial lateral oblique" (MLO) projection taken at 45 degree from the horizontal projection with the x ray tube shooting from medial towards lateral but in a 45 degree oblique orientation. This is done because this view maximizes the amount of breast tissue that can be included on the image. The 90-degree orthogonal view of "medial lateral" (ML) is generally not being used because this view cannot image the axillary portion of the breast.

Most physicians divide the breast into 4 quadrants with nipple being the origin of the axes: upper inner quadrant (UIQ), lower inner quadrant (LIQ), upper outer quadrant (UOQ) and lower outer quadrant (LOQ). Because of the non-orthogonal projections of the mammogram views, it could be difficult for the physicians and technologists to precisely localize a lesion (calcification, nodule, or mass) that is seen on the mammogram views. For instance, a lesion of the right breast that is seen lateral to the nipple on the CC view and is above the nipple on the MLO view would often be thought to be located in the upper outer quadrant can actually be in the lower outer quadrant depending upon how far it is located from the nipple.

Another system is describing the location of a lesion is a radial system. The breast is divided into parts like the face of a clock with the nipple being the center of the clock. The location of the lesion is given in terms of the clock position. For example, a lesion can be described as located in the 2 O'clock position and 4 cm away from the nipple. However, the same problem in translating the location of the lesion on the mammogram into radial coordinate exists as the Cartesian coordinate system because of the obliquity of the MLO view.

The ambiguity of the localizing lesion on the bases of mammogram can be a significant problem when the physician or technician needs to find the lesion on ultrasound. In general, the ultrasound technologists need to scan the entire half of the breast and still have problem finding the lesion. This is extremely time consuming and expensive. Often times it is difficult to be sure that a lesion seen on ultrasound is the same lesion seen on mammogram. It would be of grave consequences if a cancer seen on mammogram is called benign because ultrasound found a benign tumor (cyst or fibroadenoma) located close to the cancer. It certainly would increase the level of confidence of ultrasound findings if lesion could be more precisely localized.

U.S. Pat. No. 4,279,259, issued to D.C. Lee et al, discloses what is referred to in that patent as a "mammometer" for measuring breasts and for providing a doctor with a means for placing reference marks on the patient's breast. These marks are made by a device that uses arcs for making these determinations. The main purpose of this device is to measure the size of the women's breasts for determination of the type and size of breast implants or prosthesis. It cannot be used in conjunction with mammograms in localizing lesions within the breast because it does not take into account of how the mammograms are being performed or the direction of the x-ray beam. The Lee device utilizes a series of arcs that follow the contours of the breast. It does not utilize axes that reference how the x-ray beams are directed. The device, therefore, cannot be used to localize a lesion within the women's breast.

SUMMARY

The present invention is a template for the localization of lesions in a breast. In its broad aspects, the template includes a substrate of transparent material that includes a central marking; a horizontal line extending through the central marking; a first series of spaced lines, each line of the first series being perpendicular to the horizontal line and each line including marking indicia for indicating the distance of that line from the central marking; an oblique line extending approximately 45 degrees from the horizontal line and through the central marking; and, a second series of spaced lines, each line of the second series being perpendicular to the oblique line and each line including marking indicia for indicating the distance of that line from the central marking.

There is a right breast template and a left breast template. The appropriate template is utilized and the CC and MLO views of a mammogram are used to define a CC line and an MLO line that are plotted on that template. The intersection of these two lines is indicative of the location of the lesion. The template can then be placed over the breast of the patient and a lesion-indicative marking can be placed on the patient's skin.

Heretofore, there has been a fair degree of imprecision in localizing lesions based upon mammograms—even by the expert mammographers. Most physicians and technologists simply just perform an estimate of the location of the lesion and then scan over the area. A major advantage of the template of the present invention is that it is provides much more precision and allows the determination of the location of the lesion in a much shorter time. It also gives a greater degree of confidence in correlating lesion between ultrasound studies and mammograms.

DETAILED DESCRIPTION OF THE INVENTION

Figure 1:
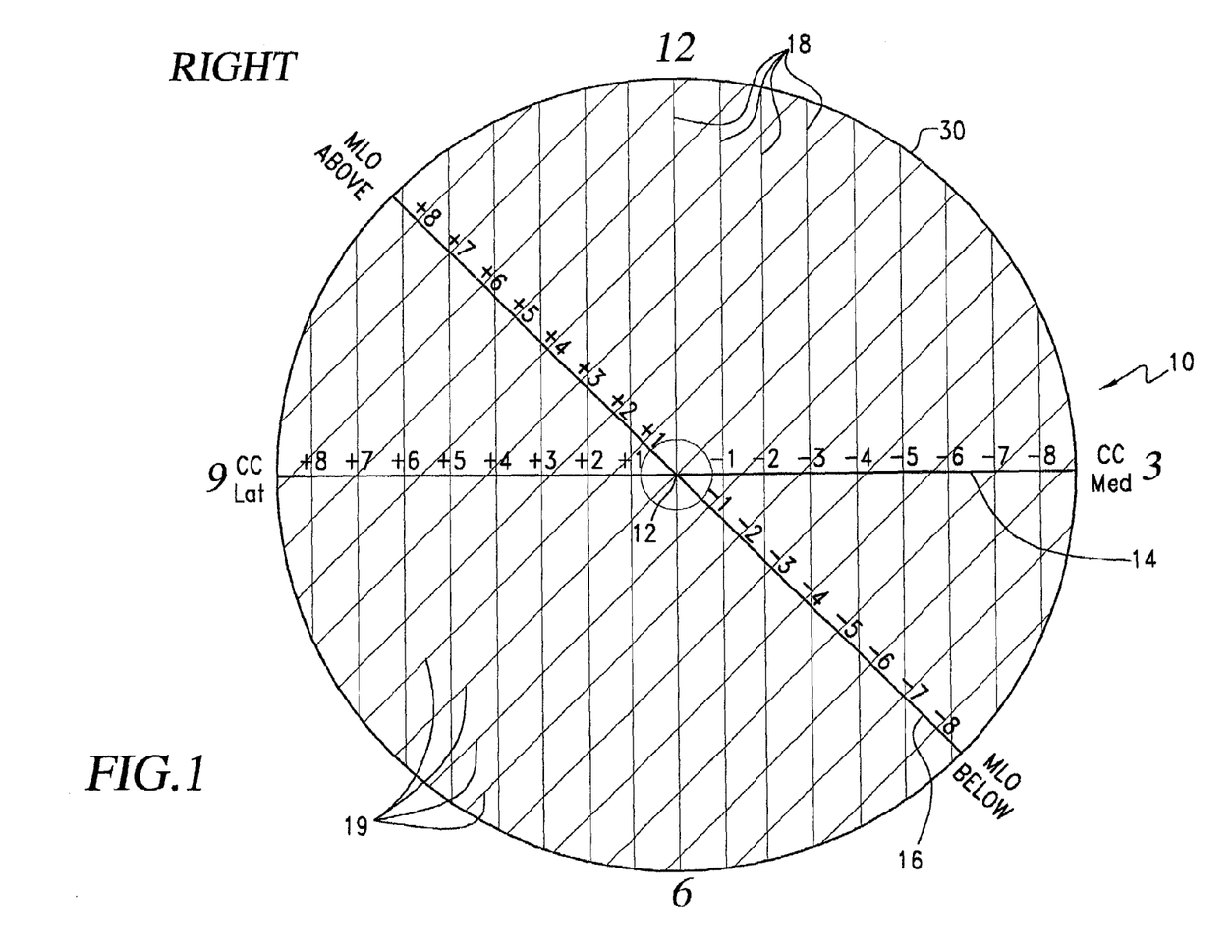
FIG. 1 is a schematic view of a right template in accordance with the principles of the present invention.
Figure 2:
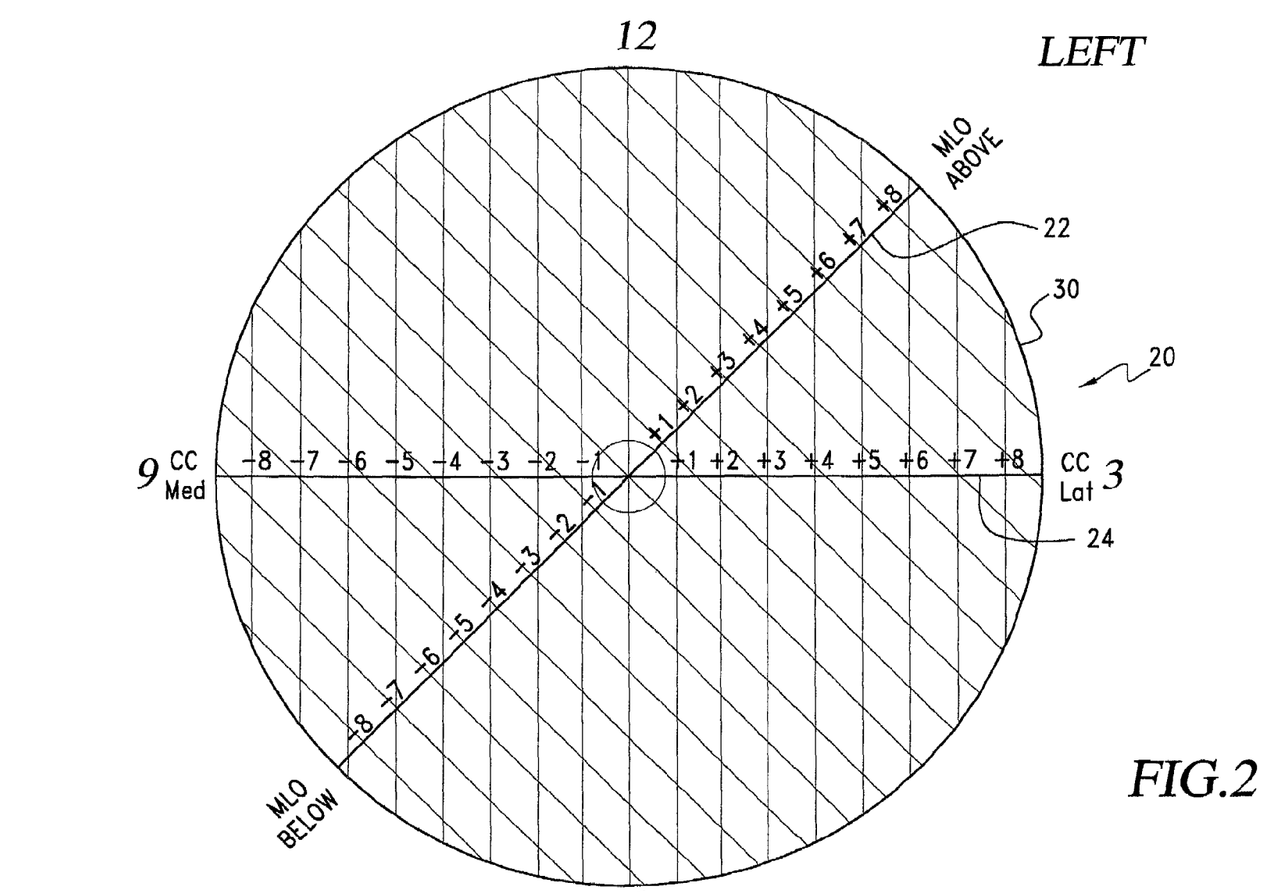
FIG. 2 is schematic view of a left template in accordance with the principles of the present invention.

Referring to the drawings and the characters of reference marked thereon FIGS. 1 and 2 illustrate preferred embodiments of the right and left templates of the present invention, designated generally as 10 and 20, respectively. Each of the templates 10, 20 comprises a substrate of transparent material, preferably flexible plastic. The substrate is preferably planar. It may be formed of various other materials such as glass. The right template 10 includes an origin or central marking 12, a horizontal line 14 extending through the central marking 12 and an oblique line 16 extending approximately a negative 45 degrees from the horizontal line 14 and through the central marking 12. These markings and the additional markings discussed hereinafter may be scratched, grooved, etched, silk screened, printed, painted, molded, or similarly fixed upon the substrate in the manner and relationships indicated to facilitate the measurements to be made.

The right template 10 includes a first series of spaced lines 18. Each line 18 of this first series is perpendicular to the horizontal line 14 and each line 18 includes marking indicia for indicating the distance of that line from the central marking 12. The horizontal line 14 defines CC view measurements. In this preferred embodiment, the spaced lines 18 are equidistantly spaced apart from each other by about 1 centimeter. The marking indicia is in a series −1, −2, −3, . . . , −8, in a positive direction from the central marking 12 and +1, +2, +3, . . . , +8 in a negative direction from the central marking.

The right template 10 also includes a second series of spaced lines 19. Each 19 of this second series is perpendicular to the oblique line 16 and each line 19 includes marking indicia. The oblique line 16 defines MLO view measurements. The spaced lines 19 are also equidistantly spaced apart from each other by about 1 centimeter. The marking indicia is in a series +1, +2, +3, . . . +8, in a superior direction from the central marking 12 and −1, −2, −3, . . . , −8 in an inferior direction from the central marking 12.

The left template and right template are similar except, as seen in FIG. 2, the oblique line 22 defining the MLO view measurements is approximately a positive 45 degrees from the horizontal line; the marking indicia on that oblique line 22 are positive in the superior direction and negative in the inferior direction; and, the marking indicia on the horizontal line 24 are positive in the positive direction and negative in the negative direction.

Although, generally, the MLO view of the mammogram is taken at 45 degrees from the horizontal, at certain times the MLO view can be taken up to 60 degrees, depending on the person's habitus. Thus, the template can be modified to take this into account. Thus, the oblique line may be in a range of about 30 degrees to 60 degrees from the horizontal line, although in the vast majority of cases 45 degrees is proper.

While measuring units of centimeters are employed in describing this invention, and in the Figures illustrating this invention, it should be clear to those skilled in the art that other units of measurement can be employed. It is believed, however, that the units chosen for purposes of illustration are that which the medical profession would prefer to use.

Both templates 10, 20 preferably include a circular border 30, primarily for aesthetic purposes.

Figure 3:
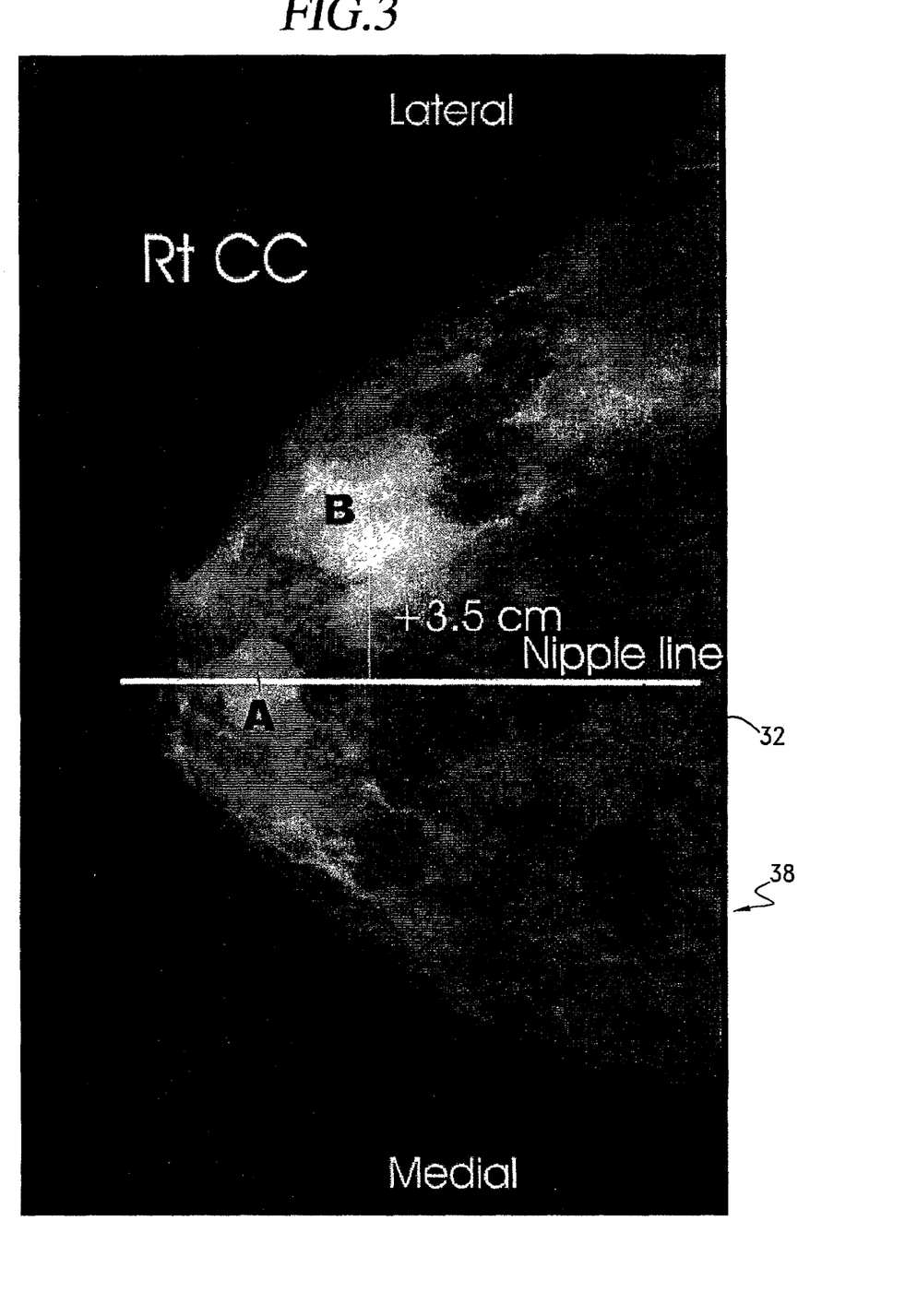
FIG. 3 is a CC view of a right breast on a mammogram, demonstrating the presence of two lesions.
Figure 4:
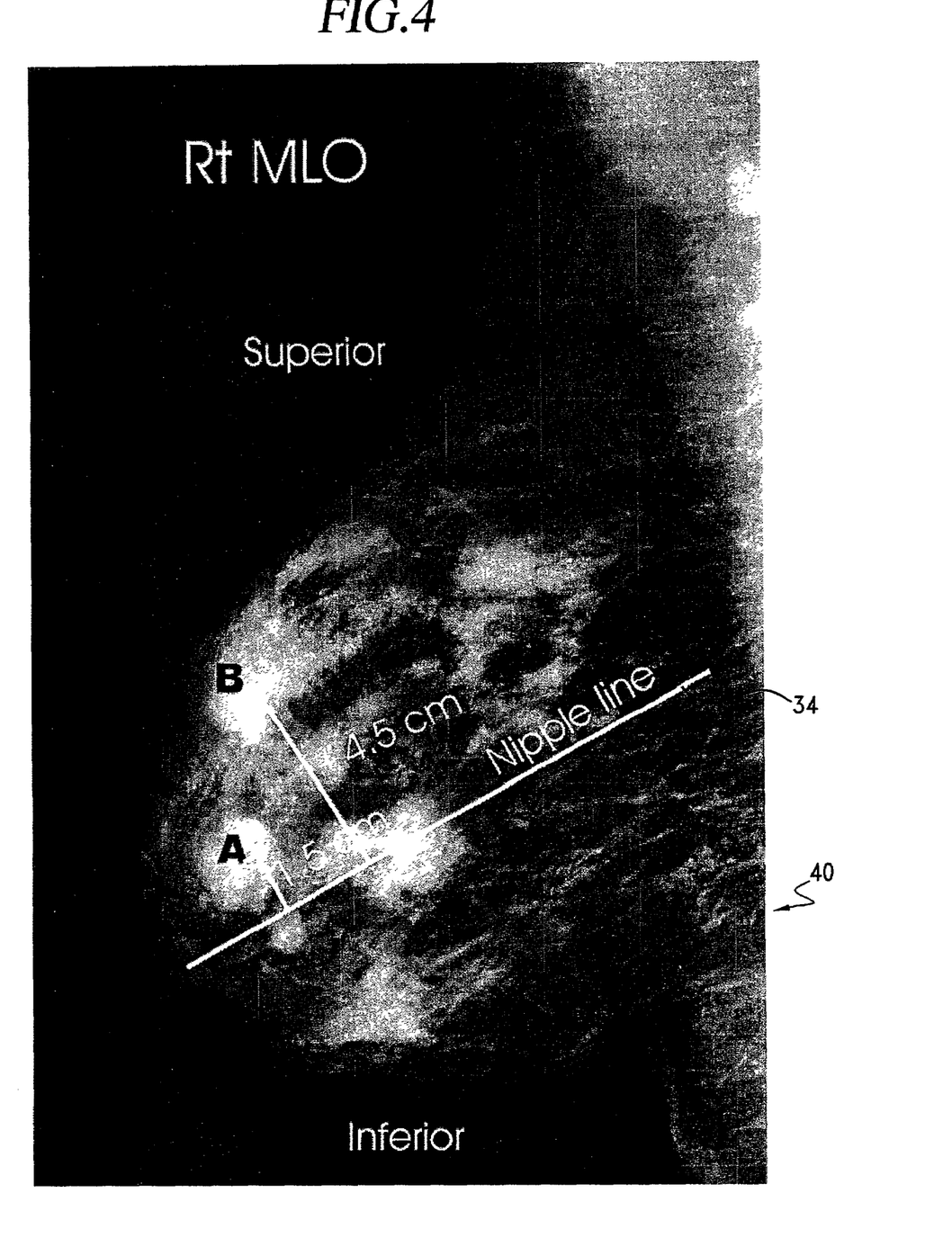
FIG. 4 is a MLO view of the same right breast on the mammogram of FIG. 4.

Referring now to FIGS. 3 and 4, in use of the templates 10, 20, a cranial caudal (CC) nipple line 32 and a medial lateral oblique (MLO) nipple line 34 are drawn on a mammogram. The CC nipple line 32 is on a CC view 38 (FIG. 3) and extends through the nipple toward the chest wall, bifurcating the breast into a medial half and a lateral half. The MLO nipple line 34 is on an MLO view 40 (FIG. 4) and extends through the nipple toward the chest wall, bifurcating the breast into a superior half and an inferior half. Drawing the MLO nipple line 34 is somewhat more difficult than the CC nipple line 32 because the breast is usually slanted superiorly towards the chest wall dividing the breast into a slightly larger more triangular superior half and a slightly smaller and more rounded inferior half.

The mammogram demonstrates the presence of two lesions, designated "A" and "B". The shortest distance from each lesion to the CC nipple line 32 is measured and the shortest distance from the lesion to the MLO nipple line 34 is also measured. For the right breast the distance to the CC nipple line 32 is deemed a negative value if the lesion is located medial to the CC nipple line and deemed a positive value if the lesion is located lateral to the CC nipple line. The distance to the MLO nipple line 34 is deemed a positive value if the lesion is located superior to the MLO nipple line and deemed a negative value if the lesion is located inferior to the MLO nipple line.

Figure 5:
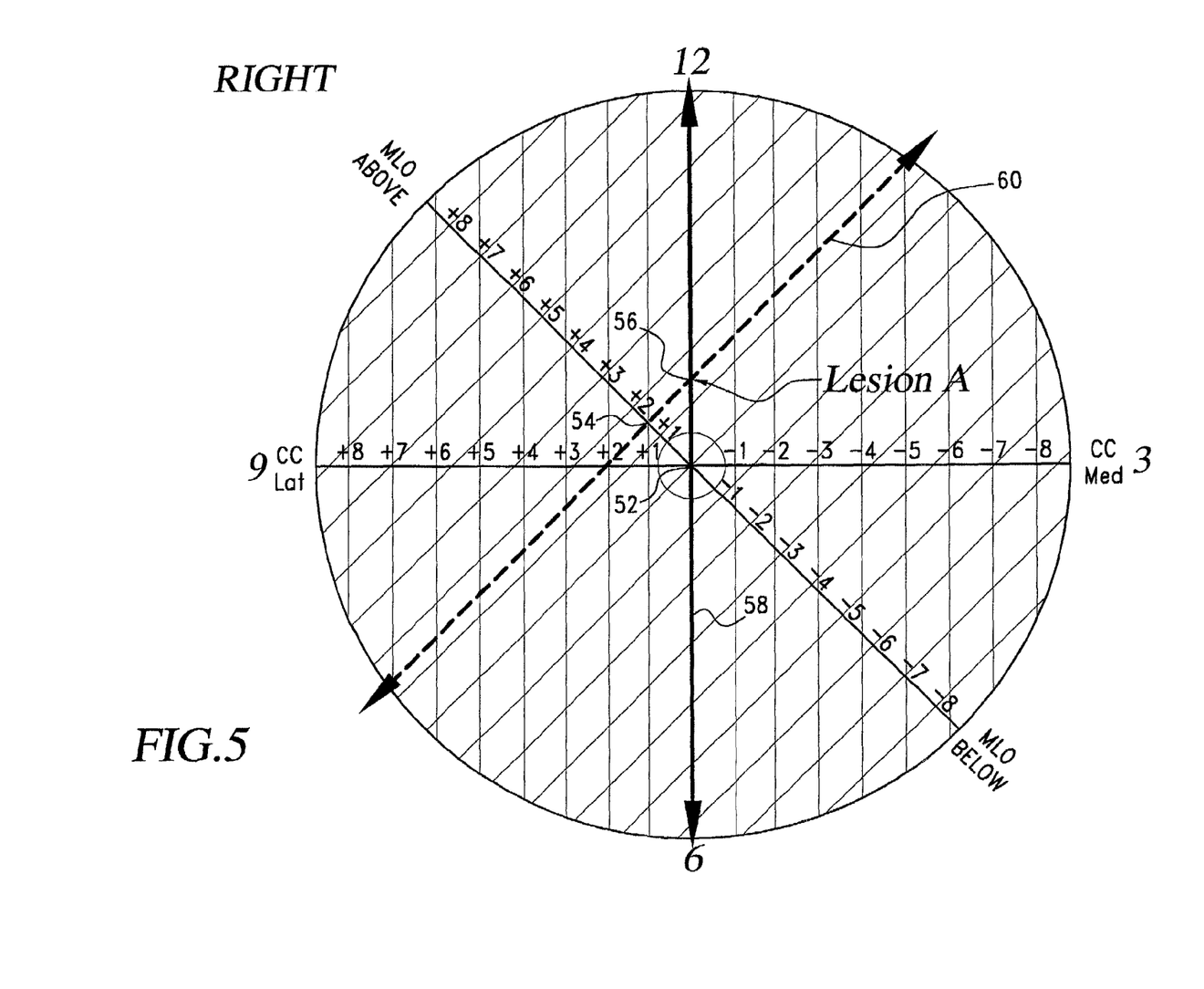
FIG. 5 is a schematic illustration showing the plotting of lines on a right template to show the method of using the template to localize a first of the two lesions.

Referring now to FIG. 5, the measurements for Lesion A are plotted on an appropriate template, in this case a right breast template 50. Care must be taken to be sure to use the correct template for the correct breast (i.e. right vs. left). The measured distances are plotted as a CC point 52 along the horizontal line (in this case at the origin since Lesion A happened to be on the CC nipple line) and a MLO point 54 along the oblique line. Care must be taken to be sure that the proper coordinate definition (i.e. medial vs. lateral and superior vs. inferior) is used.

The intersection 56 of a CC line 58 (which in this case happens to correspond with the y-axis) and a MLO line 60 is plotted. The CC line 58 is a perpendicular line to the horizontal line that intersects the horizontal line at the CC point 52. The MLO line 60 is a perpendicular line to the oblique line that intersects that MLO line 60 at the MLO point 54. The intersection 56 is indicative of the location of the lesion. An X may be placed where these two lines meet.

Figure 6:
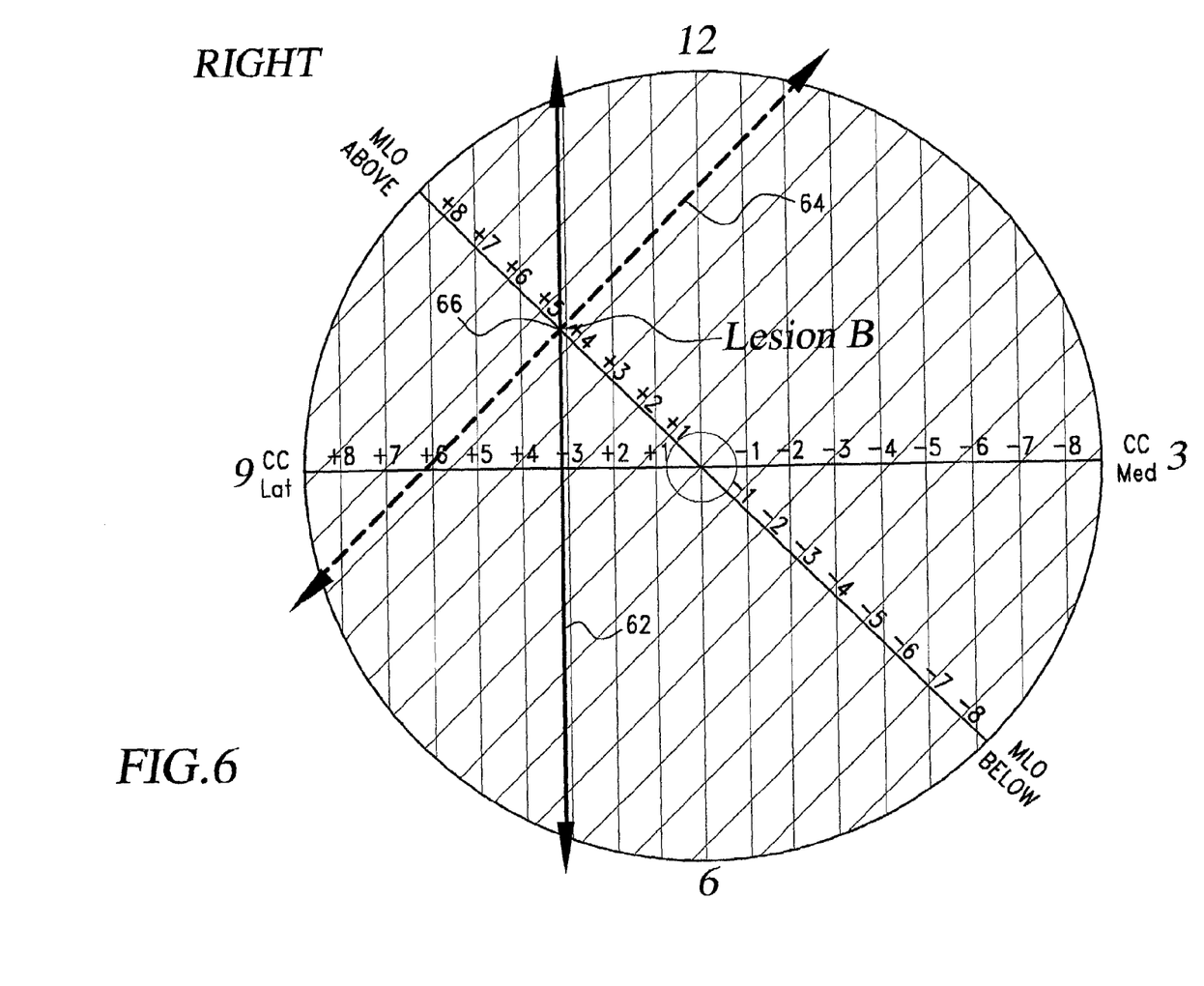
FIG. 6 is a schematic illustration showing the plotting of lines on a right template to show the method of using the template to localize a second of the two lesions.

FIG. 6 illustrates the plotting of Lesion B on the right template. The CC line 62 is positioned at +3.5 cm and the MLO line 64 is positioned at +4.5 cm. The intersection 66 denotes the position of Lesion B.

A marker, i.e. BB, or other suitable marking means may be placed on the underside of the template. The template may then be placed over the patient's breast with the central marking directly over the nipple. A lesion-indicative mark is then placed over the patient's skin marking the location of the lesion. This may be accomplished by pressing on the template to leave an impression. The template is then removed. Ultrasound scanning or another desired procedure can then be performed. The marking method may involve use of holes within the template into which a marking instrument may extend in order to provide the necessary mark.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters patent of the United States is:

1. A method for localizing a lesion in a breast, comprising the steps of:

a) drawing a cranial caudal (CC) nipple line and a medial lateral oblique (MLO) nipple line on a mammogram, said CC nipple line being on a CC view and extending through the nipple toward the chest wall, bifurcating the breast into a medial half and a lateral half, said MW nipple line being on an MLO view and extending thmugh the nipple toward the chest wall, bifurcating the breast into a superior half and an interior half;
b) measuring the shortest distance from a lesion to said CC nipple line and the shortest distance from the lesion to said MLO nipple line;
c) plotting said measured distances on a template, said template comprising a substrate of transparent material, comprising:
  i. a central marking;
  ii. a horizontal line extending through said central marking, said horizontal line defining CC view measurements;
  iii. a first series of spaced lines, each line of said first series being pSrpendicular to said horizontal line and each line including marking indicia for indicating the distance of that line from the central marking;
  iv. an oblique line extending approximately 45 degrees from said horizontal line and through said central marking, said oblique line defining MLO view measurements; and
  v. a second series of spaced lines, each line of said second series being perpendicular to said oblique line and each line including marking indicia for indicating the distance of that line from the central marking,
  said measured distances being plotted as a CC point along said horizontal line and a MLO point along said oblique line;
d) plotting the intersection of a CC line and a MLO line, the CC line being a perpendicular line to said horizontal line and intersecting said horizontal line at said CC point and the MLO line being a perpendicular line to said oblique line and intersecting said MLO line at said MLO point, said intersection being indicative of the location of said lesion;
e) placing said template over a breast with said central marking directly over the nipple; and,
f) placing a lesion-indicative marking over the patient's skin marking the location indicative of said lesion.

2. The method of claim 1, wherein:
said step of measuring the shortest distance from a lesion to said CC nipple line comprises deeming said measurement as being a positive value if the lesion is located medial to the CC nipple line and deeming it a negative value if the lesion is located lateral to the CC nipple line; and
said step of measuring the shortest distance from a lesion to said MLO nipple line comprises deeming said measurement as being a positive value if the lesion is located superior to the MLO nipple line and deeming it a negative value if the lesion is located inferior to the MLO nipple line.

3. A method for localizing a lesion in a breast, comprising the steps of:
a) drawing a cranial caudal (CC) nipple line and a medial lateral oblique (MLO) nipple line on a mammogram, said CC nipple line being on a CC view and extending through the nipple toward the chest wall, bifurcating the breast into a medial half and a lateral half, said MLO nipple line being on an MLO view and extending through the nipple toward the chest wall, bifurcating the breast into a superior half and an interior halft
b) measuring the shortest distance from a lesion to said CC nipple line and the shortest distance from the lesion to said MLO nipple line;
c) plotting said measured distances on a template, said template comprising a substrate of transparent material, comprising:
  i. a central marking;
  ii. a horizontal line ext6nding through said central marking, said horizontal line defining CC view measurements;
  iii. a first series of spaced lines, each line of said first series being perpendicular to said horizontal line and each line including marking indicia for indicating the distance of that line from the central marking;
  iv. an oblique line extending in a range of about 30 to 60 degrees from said horizontal line and through said central marking, said oblique line defining MLO view measurements; and
  v. a second series of spaced lines, each line of said second series being perpendicular to said oblique line and each line including marking indicia for indicating the distance of that line from the central marking,
  said measured distances being plotted as a CC point along said horizontal line and a MLO point along said oblique line;
d) plotting the intersection of a CC line and a MLO line, the CC line being a perpendicular line to said horizontal line and intersecting said horizontal line at said CC point and the MLO line being a perpendicular line to said oblique line and intersecting said MLO line at said MLO point, said intersection being indicative of the location of said lesion;
g) placing said template over a breast with said central marking directly over the nipple; and,
h) placing a lesion-indicative marking aver the patient's skin marking the location indicative of said lesion.

* * * * *

UNITED STATES PATENT AND TRADEMARK OFFICE
CERTIFICATE OF CORRECTION

PATENT NO. : 7,124,760 B2  
APPLICATION NO. : 10/150344  
DATED : October 24, 2006  
INVENTOR(S) : Wong Page 1 of 1

It is certified that error appears in the above-identified patent and that said Letters Patent is hereby corrected as shown below:

Column 5, Line 5 – delete "MW" and insert therefor --MLO--

Column 5, Line 7 – delete "thmugh" and insert therefor --through--

Column 5, Line 20 – delete "pSrpendicular" and insert therefor --perpendicular--

Column 6, Line 14 – delete "halft" and insert therefor --half--

Column 6, Line 22 – delete "ext6nding" and insert therefor --extending--

Column 6, Line 51, – delete "aver" and insert therefor --over--

Signed and Sealed this

Sixteenth Day of January, 2007

JON W. DUDAS  
*Director of the United States Patent and Trademark Office*